US00PP16201P3

(12) United States Plant Patent
Hasegawa

(10) Patent No.: US PP16,201 P3
(45) Date of Patent: Jan. 10, 2006

(54) CARNATION PLANT CALLED 'CFPC ANGELICA'

(50) Latin Name: *Dianthus caryophyllus*
Varietal Denomination: CFPC Angelica

(76) Inventor: Oscar T. Hasegawa, 1721 Burlington Dr., Salinas, CA (US) 93906

( * ) Notice: Subject to any disclaimer, the term of this patent is extended or adjusted under 35 U.S.C. 154(b) by 74 days.

(21) Appl. No.: 10/837,431

(22) Filed: Apr. 30, 2004

(65) Prior Publication Data

US 2005/0246810 P1 Nov. 3, 2005

(51) Int. Cl.
*A01H 5/00* (2006.01)

(52) U.S. Cl. ..... Plt./273

(58) Field of Classification Search ..... Plt./273
See application file for complete search history.

*Primary Examiner*—Anne Marie Grunberg
(74) *Attorney, Agent, or Firm*—Christie, Parker & Hale, LLP

(57) ABSTRACT

A new and distinct variety of carnation plant characterized by a white background with pencil and picotee pink flower color.

1 Drawing Sheet

Botanical classification: The present invention relates to a new and distinct variety of hybrid *Dianthus caryophyllus*. The varietal denominator of the new variety is 'CFPC Angelica'.

BACKGROUND OF THE INVENTION

The present invention relates to a new and distinct variety of carnation plant, named 'CFPC Angelica', which was originated by me from a cross made in a controlled breeding program. The female, or seed, parent is unpatented and identified as 970101; the male, or pollen, parent is unpatented and identified as 970118. The primary objective of the controlled breeding program was to produce a cultivar having a flower of new color.

SUMMARY OF THE INVENTION

Among the novel characteristics possessed by the new variety which distinguishes it is a distinctive white background with pencil (radial streaks or lines along the length of the petals) and picotee pink flower color, which retains its color without fading. The present inventor is unaware of any other pot carnation commercially available in this color. When grown in 4½ inch plastic pots in Salinas, Calif., plant diameter averages 7 inches. Pinched plants are about 7 inches tall and flowers are about 2 inches average diameter with a crown higher than about 1 inch. Foliage is about 3¼ inches long and about 5/16 inches wide.

Asexual reproduction by propagation by side shoot cuttings of the new variety as performed in Salinas, Calif., shows that the foregoing and other distinguishing characteristics come true to form and are established and transmitted through succeeding propagations.

COMPARISON TO PARENTS

'CFPC Angelica' has a distinctive white background with pencil and picotee pink flower color.

The female parent 970101 has a yellow picotee lavender flower color, while the male parent 970118 has a white picotee pink flower color.

BRIEF DESCRIPTION OF ILLUSTRATIONS

The accompanying photographic illustration shows a typical specimen of the new variety in color as nearly true as it is reasonably possible to make in a color illustration of this character.

DESCRIPTION OF THE NEW VARIETY

Referring now specifically to the new and distinct variety of carnation plant the following is a detailed description of 'CFPC Angelica', at approximate age 121 days, with color description where indicated by reference to The Royal Horticultural Society Colour Chart, except where common terms of color definition are employed.

The new variety of carnation plant as herein described may vary in slight detail due to climatic, soil and cultural conditions under which the variety may be grown, the present description being of the variety as grown at Salinas, Calif.

Plant:
- *Height.*—About 7 inches tall.
- *Growing habit.*—Semi-upright.
- *Blooming habit.*—As a spray when grown in a pot; blooming time, approximately 110 days.
- *Shelf life.*—Approximately 21 days in bloom.
- *Rooting time.*—About 18 days.
- *Breaking action.*—Good.
- *Mutation prone.*—No.
- *Disease resistance.*—Resistant to *Fusarium oxysporum* and *Fusarium graminearum.*

Foliage:
- *Color.*—Upper side: near 136A; lower side: near 137A.
- *Size.*—Length: about 3¼ inches; width: about 5/16 inches.
- *Stem color.*—Near 138B.

Bud:
- *Shape.*—Ovoid.
- *Color.*—Near 138B.
- *Size.*—Length: about 1 inch; diameter: about 7/16 inches.

Calyx:

*No. of lobes* (*sepals*).—Five.

*Size.*—Length: about ¼ inches; width: about 3/16 inches.

*Color.*—Outside: near 138B; inside: near 138D.

Bloom:

*Size.*—Diameter (average): about 2 inches; depth (average): about 1 inch.

*Borne.*—As a spray.

*Color.*—General tonality: white background pencil and picotee pink; Upper side: near 155D or whiter; Lower side: near 155D or whiter; Center: near 155D or whiter; Outer petals: near 62B.

*Keeping quality.*—Very good over three weeks.

*Fragrance.*—Slight.

Petalage:

*Number.*—Twenty-five to twenty-six.

*Outer petals.*—Length: about 1⅞ inches; Width: about 1⅜ inches.

*Central petals.*—Length: about 1⅝ inches; Width: about 1 inch.

*Texture.*—Smooth.

*Appearance.*—Shiny.

*Form.*—Fan-shaped.

Reproductive organs:

*Stamen.*—None (male sterile).

*Anthers.*—None.

*Filaments.*—None.

*Pistil.*—Number: one (trilobed). Color: whiter than 155D.

*Stigma.*—Number: 3 (trilobed); Color: 62D at tips of stigma.

*Fertility.*—Male: sterile.

*Ovary.*—Shape: conical; Color: base near 157D, body near 144D, apex near 144D.

I claim:

1. A new and distinct variety of carnation plant identified as 'CFPC Angelica', substantially as shown and described.

* * * * *

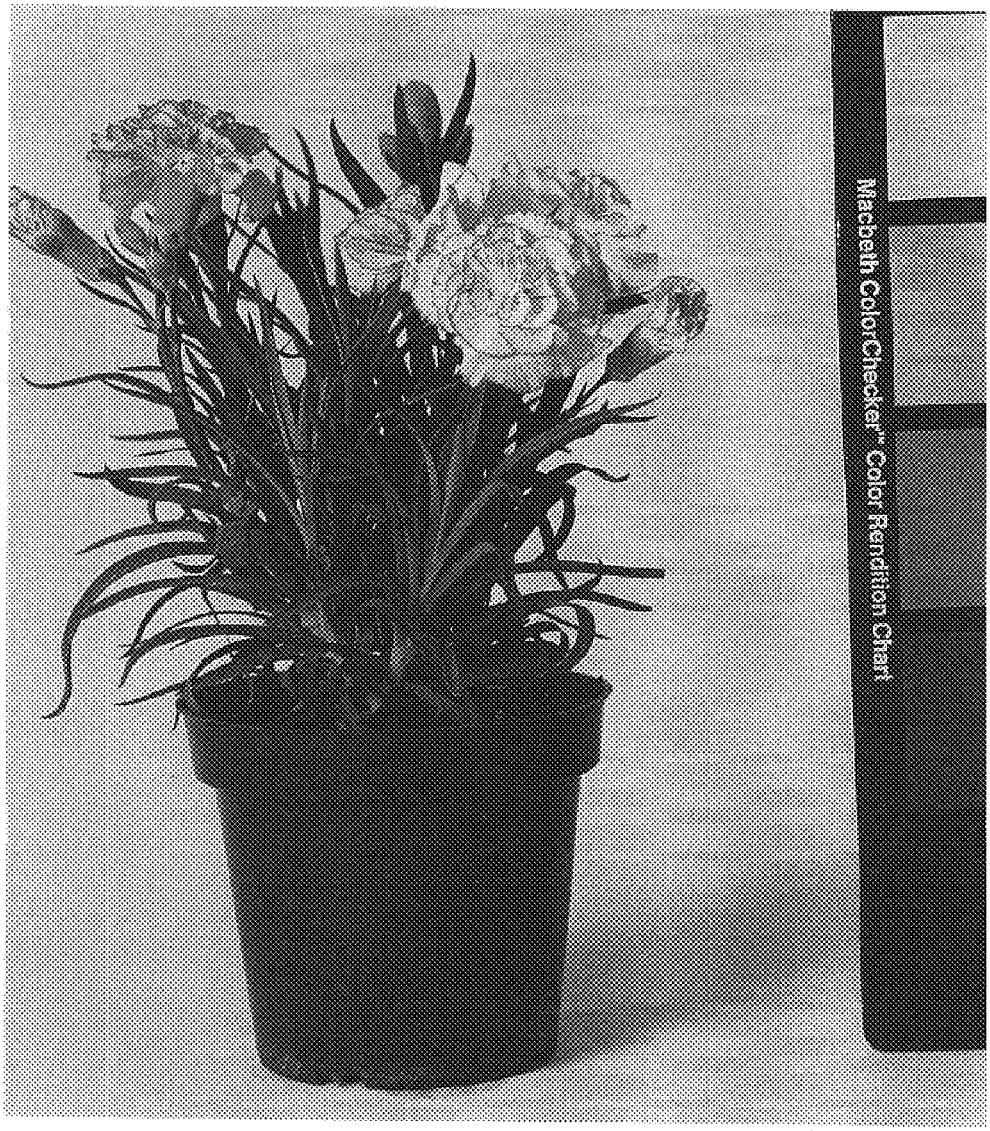
Macbeth Color Checker™ Color Rendition Chart